(12) United States Patent
Usala

(10) Patent No.: US 6,261,587 B1
(45) Date of Patent: Jul. 17, 2001

(54) METHODS FOR INCREASING VASCULARIZATION AND PROMOTING WOUND HEALING

(76) Inventor: Anton-Lewis Usala, 237 Buckingham Dr., Winterville, NC (US) 28590

( * ) Notice: Subject to any disclaimer, the term of this patent is extended or adjusted under 35 U.S.C. 154(b) by 0 days.

(21) Appl. No.: 09/337,959

(22) Filed: Jun. 22, 1999

Related U.S. Application Data

(63) Continuation-in-part of application No. 09/113,437, filed on Jul. 10, 1998.

(51) Int. Cl.$^7$ ................................................. A61F 2/02
(52) U.S. Cl. .......................... 424/426; 424/424; 424/425
(58) Field of Search .................................. 424/426, 424, 424/425

(56) References Cited

U.S. PATENT DOCUMENTS

| | | |
|---|---|---|
| 4,198,479 | 4/1980 | Tytell et al. . |
| 4,477,567 | 10/1984 | Healy et al. . |
| 4,520,821 | 6/1985 | Schmidt et al. . |
| 4,657,866 | 4/1987 | Kumar . |
| 4,863,856 | 9/1989 | Dean, Jr. et al. . |
| 4,902,295 | 2/1990 | Walthall et al. . |
| 4,950,483 | * 8/1990 | Ksander et al. . |

(List continued on next page.)

FOREIGN PATENT DOCUMENTS

| | | |
|---|---|---|
| 4431598 | 3/1996 | (DE) . |
| 0 213 908 | 3/1987 | (EP) . |
| 0 363 125 | 10/1989 | (EP) . |
| 0 481 791 A2 | 4/1992 | (EP) . |
| 0 526 756 | 2/1993 | (EP) . |
| 0 564 786 | 10/1993 | (EP) . |
| WO 91/09119 | 6/1991 | (WO) . |
| WO 92/19195 | 11/1992 | (WO) . |
| WO 93/00441 | 1/1993 | (WO) . |
| WO 93/24112 | 12/1993 | (WO) . |
| WO 94/03154 | 2/1994 | (WO) . |
| WO 94 08702 | 4/1994 | (WO) . |
| WO 94/15589 | 7/1994 | (WO) . |
| WO 95/14037 | 5/1995 | (WO) . |
| WO 95/29231 | 11/1995 | (WO) . |
| WO 97 20569 | 6/1997 | (WO) . |
| WO 97 39107 | 10/1997 | (WO) . |
| WO 98/04681 | 2/1998 | (WO) . |
| WO 98/16629 | 4/1998 | (WO) . |

OTHER PUBLICATIONS

Donofrio, "The Effects of Growth Factors on Proliferation of Adult Porcine In Vitro", Department of Biology, East Carolina University (May 1997).

Hubbell, et al., "Tissue Engineering," Chemical & Engineering News, (Mar. 13, 1995), pp. 42–54.

Metrakos, et al., "Collagen Gel Matrix Promotes Islet Cell Proliferation", Transplantation Proceedings, vol. 26, No. 6 (Dec. 1994) pp. 3349–3350.

Mandel et al., "Organ Culture of Fetal Mouse and Fetal Human Pancreatic Islets for Allograftting," Diabetes, vol. Suppl. 4 (Aug. 1982), pp. 39–47.

Isner et al., Therapeutic Angiogenesis, Frontiers in Bioscience, May 5, 1998, pp. e–49–69, vol. 3.

*Primary Examiner*—Carlos A. Azpuru
(74) *Attorney, Agent, or Firm*—Alston & Bird LLP

(57) ABSTRACT

The present invention provides a method of stimulating vascularization at a site in a mammal, said method comprising contacting said site with a matrix comprising gelatin and a nitric oxide inhibitor. The gelatin is preferably denatured collagen. The nitric oxide inhibitor may be a sulfonated moiety. The inhibitor may be an L-arginine analog, such as aminoguanidine, N-monoethyl L-arginine, N-nitro-L-arginine and D-arginine. The matrix may further comprise a nitric oxide scavenger, such as dextran, heparin, cysteine and cystine.

57 Claims, 4 Drawing Sheets

U.S. PATENT DOCUMENTS

| | | |
|---|---|---|
| 4,978,616 | 12/1990 | Dean, Jr. et al. . |
| 4,997,753 | 3/1991 | Dean, Jr. et al. . |
| 5,021,349 | 6/1991 | Derouet et al. . |
| 5,100,783 | 3/1992 | Dean, Jr. et al. . |
| 5,116,753 | 5/1992 | Beattie et al. . |
| 5,132,223 | 7/1992 | Levine et al. . |
| 5,405,772 | 4/1995 | Ponting . |
| 5,605,938 | 2/1997 | Roufa et al. . |
| 5,645,591 | 7/1997 | Kuberasampeth et al. . |
| 5,672,361 | 9/1997 | Halberstadt et al. . |
| 5,681,587 | 10/1997 | Halberstadt et al. . |
| 5,716,404 | 2/1998 | Vacanti et al. . |
| 5,824,331 | 10/1998 | Usala . |
| 5,830,492 | 10/1998 | Usala . |
| 5,834,005 | 11/1998 | Usala . |
| 5,840,059 | 11/1998 | March et al. . |
| 5,855,617 | 1/1999 | Orton . |

* cited by examiner

METHODS FOR INCREASING VASCULARIZATION AND PROMOTING WOUND HEALING

CROSS-REFERENCE TO RELATED APPLICATIONS

This application is a continuation-in-part of application Ser. No. 09/113,437, filed Jul. 10, 1998, which is incorporated herein by reference.

FIELD OF INVENTION

The invention is drawn to methods and compositions for improving vascularization in mammals. Additionally, the compositions find use in wound healing.

BACKGROUND OF THE INVENTION

Blood vessels are assembled by two processes known as vasculogenesis and angiogenesis. In vasculogenesis, a primitive vascular network is established during embryonic development from endothelial cell precursors called angioblasts. Angiogenesis involves preexisting vessels sending out capillary buds or sprouts to produce new vessels. Angiogenesis is an important process critical to chronic inflammation and fibrosis, to tumor cell growth, and to the formation of collateral circulation. Angiogenesis is involved in the normal process of tissue repair.

Tissue destruction, with damage to both parenchymal cells and stromal framework, occurs in inflammation. Repair to the tissue cannot be accomplished solely by regeneration of parenchymal cells, even in organs whose cells are able to regenerate. Attempts at repairing tissue damage occur by replacement of non-regenerated cells by connective tissue, which in time produces fibrosis and scarring.

After inflammation, repair of the tissue immediately begins. Fibroblasts and vascular endothelial cells began proliferating to form granulation tissue. Granulation tissue is characterized by the formation of new small blood vessels and the proliferation of fibroblasts. The new vessels are leaky and allow the passage of proteins and red blood cells into the extravascular space.

The inflammatory response is closely intertwined with the process of repair. Inflammation serves to destroy, dilute, or wall off the injurious agent. In turn, inflammation sets into motion a series of events that heal and reconstitute the damaged tissue. While repair begins during the early phases of inflammation, it reaches completion only after the injurious influence has been neutralized. During repair, the injured tissue is replaced by regeneration of native parenchymal cells, by filling of the defect with fibroblastic tissue, commonly known as scarring.

The inflammatory response occurs in the vascularized connective tissue. Circulating cells such as neutrophils, monocytes, eosinophils, lymphocytes, basophils, and platelets are involved. Connective tissue cells are the mast cells, which surround blood vessels, the connective tissue fibroblasts, and occasional resident macrophages and lymphocytes.

Progress has been made in transplant technology. New strategies on the horizon include the creation of man-made tissues or organs. However, the transplanted tissue or organ requires a blood supply. Thus, methods are needed for promoting vascularization in sites of interest.

SUMMARY OF THE INVENTION

Compositions and methods for stimulating and maintaining vascularization at predetermined sites in a host organism are provided. The method includes contacting the site with the matrix of the present invention wherein the matrix comprises denatured collagen, dextran and nitric oxide inhibitors. The matrix is useful in any setting where the host organism may benefit from an increased blood supply. Thus, the methods are useful in the treatment of diseases or conditions that benefit by increased blood circulation, in transplant therapies, wound healing and the like.

DETAILED DESCRIPTION OF THE INVENTION

Figure 1:
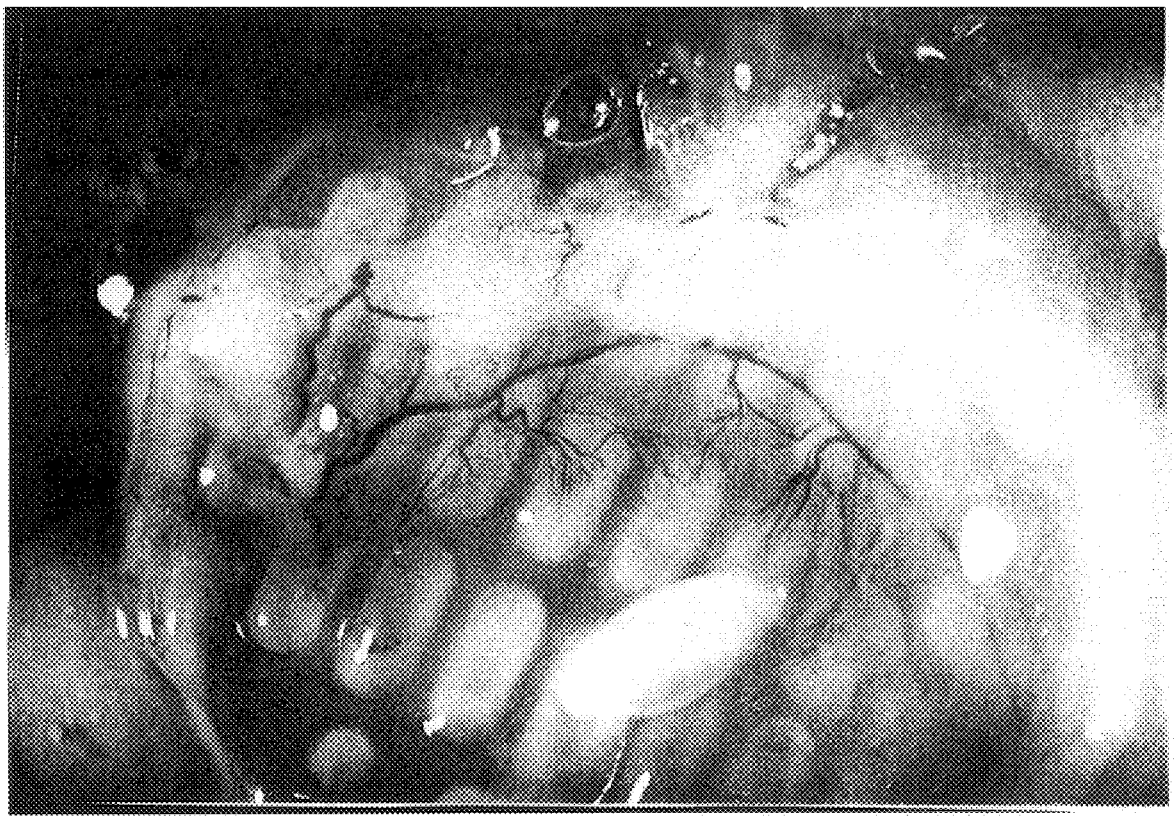
FIG. 1 shows blood vessel formation around a device 6 weeks post implant.

The present invention provides a hydrogel matrix which is useful for promoting vascularization. The matrix has been previously described in U.S. application Ser. No. 09/113, 437, and U.S. Pat. No. 5,824,331, herein incorporated by reference. The matrix is able to immobilize water at appropriate storage temperatures and provide binding sites for cells that stimulate growth in terminal cell types, such as beta cells.

The matrix of the invention stimulates local blood vessel growth within a thin fibrous capsule or sheet. While the invention is not bound by any mechanism of action, it is hypothesized that the matrix collagen fragments serve as both a scaffolding and stimulus for fibroblasts and new, physiologic blood vessel expansion, without stimulating immune cell response. Upon breaking the intimal basement membrane of any tissue, polar amino acid sequences are exposed. For example, injection into a muscle with a needle will provide this tearing. The matrix contains denatured collagen fragments loosely bound to dextran, which bind to the exposed polar surface of the basement membrane. Highly polar amino acid additives may be included in the matrix which aid in binding of the collage fragments to the polar surface of the membrane. Within a few hours, the aqueous portion of the matrix is absorbed by the surrounding tissue, leaving only the peptide fragments bound to the exposed polar surfaces. The nitric oxide inhibitors and scavengers present in the matrix inhibit the attraction and activation of immune cells to the area. The denatured connective tissue monomers that are co-polymerized with the dextran component of the matrix provide scaffolding required for endothelial proliferation.

The connective tissue fragments resemble immature collagen in that they are not cross-linked in the large triple standard helix found in mature collagen. In utero, single-stranded collagen monomers are laid down first, then cross-linked with other monomers to form mature collagen. This process is followed by cellular binding and differentiation, as well as new blood vessel supply. Because collagen sequences are conserved in mammalian species, it is believed that the matrix collagen fragments serve both a scaffolding and as a stimulus for fibroblasts and new physiologic blood vessel expansion, without stimulating immune cell response.

The matrix of the present invention is a combination of a gelatin component and a liquid composition. The gelatin acts as a substrate for cellular attachment. The preferred gelatin component is denatured collagen. Denatured collagen contains polar and non-polar amino acids that readily form a gel based on amine, carboxyl group, hydroxyl group, and sulfhydryl group interactions. The matrix is designed to be in a free flowing or liquid phase at host body temperature in order to provide maximum diffusion across the membrane in vivo. The matrix remains in solid phase at the lower storage temperatures, such as 4° C.

Boiling or otherwise treating intact collagen to form denatured collagen breaks covalent chemical bonds and increases the number of heat sensitive hydrogen bonds and dipole moment attractions. By replacing the covalent chemical bonds with temperature sensitive bonds and attractions, the desired cells can be embedded in a solid matrix formulation at colder temperatures for sustained storage. Boiling or otherwise treating intact collagen breaks the tightly coiled helical tropocollagen subunits and causes the subunits to open up into separate peptide chains. These uncoiled strands provide multiple binding areas for cells to attach.

The gelatin is present at a concentration of about 0.01 to about 40 mM, preferably about 0.05 to about 30 mM, most preferably about 1 to 5 mM. Advantageously, the gelatin concentration is approximately 1.6 mM. The above concentrations provide a solid phase at storage temperature and a liquid phase at transplant or injection temperature.

The gelatin component of the matrix of the present invention is mixed with a liquid composition. The liquid composition is preferably based upon a standard culture medium, such as Medium 199, supplemented with additives and additional amounts of some medium components, such as supplemental amounts of polar amino acids as described above.

The matrix of the present invention may further include a nitric oxide scavenger. For example, L-cysteine acts as a nitric oxide scavenger and appears to obscure immune recognition sites by binding or docking to the surface of the cells. L-cysteine also provides disulfide linkages which increases the matrix's resistance to force and further protects the cells contained therein. Nitric oxide (NO) is a pleiotropic mediator of inflammation. NO plays an important role in vascular function during inflammatory responses. NO is a soluble gas produced by endothelial cells, macrophages, and specific neurons in the brain. NO is active in inducing the inflammatory response.

The final concentration of L-cysteine is about 5 to about 5,000 $\mu$M, preferably about 10 to about 800 $\mu$M, most preferably about 100 to about 800 $\mu$M. In one embodiment, the final concentration is about 20 $\mu$M.

The matrix of the present invention preferably comprises a nitric oxide inhibitor. For example, aminoguanidine is an L-arginine analogue and acts as a nitric oxide inhibitor. Other L-arginine analogues that act as nitric oxide inhibitors could also be used in the present invention. The final concentration of aminoguanidine is about 5 to about 500 $\mu$M, preferably about 10 to about 100 $\mu$M, most preferably about 15 to about 25 $\mu$M. In one embodiment, the final concentration is about 20 $\mu$M.

In order to increase cell binding, intact collagen may be added in small amounts to provide an additional binding network for the cells contained in the matrix. The final concentration of intact collagen is from about 0 to about 5 mM, preferably 0 to about 2 mM, most preferably about 0.05 to about 0.5 mM. In one embodiment, the concentration of intact collagen is about 0.11 mM.

The matrix of the present invention may optionally include a divalent chelator which increases the rigidity of the matrix by removing inhibition of —$NH_2$ to —COOH hydrogen bonding. The divalent chelator also protects against microbial contamination of the matrix. A preferred divalent chelator is EDTA. The concentration range for the chelator is about 0 to about 10 mM, preferably 1 to about 8 mM, most preferably about 2 to about 6 mM. In a preferred embodiment, EDTA is present at a concentration of about 4 mM. Conventional antibiotics can also be added to further protect against microbial contamination.

While the matrix of the invention does not require the presence of sera, albumin or other nutrient sources may be added to the matrix if desired. Preferably, the albumin used is of the same species as the cells contained within the matrix. As described above, use of the same species albumin promotes increased robustness in the cells contained in the matrix. The concentration of albumin is about 0 to about 2% by volume, preferably 0 to about 0.5% by volume, most preferably about 0 to about 0.1% by volume. In a preferred embodiment, the concentration of albumin is about 0.05% by volume.

The matrix may contain an effective amount of polar amino acids therein. The polar amino acids may be selected from the group consisting of arginine, lysine, histidine, glutamic acid, and aspartic acid, or other amino acids or other polar chemicals. An effective amount is the amount necessary to increase the rigidity of the matrix and further enhance binding of the collagen fragment to the polar surface of the basement membrane. In one embodiment, the concentration of polar amino acids is raised to a final concentration of between about 3 to about 150 mM, preferably about 10 to about 65 mM, and more preferably about 15 to about 40 mM.

Advantageously, the added polar amino acids comprise L-glutamic acid, L-lysine, and arginine. The final concentration of L-glutamic acid is about 2 to about 60 mM, preferably about 5 to about 40 mM, most preferably about 10 to about 20 mM. In one embodiment, the concentration of L-glutamic acid is about 15 mM. The final concentration of L-lysine is about 0.5 to about 30 mM, preferably about 1 to about 15 mM, most preferably about 1 to about 10 mM. In one embodiment, the concentration of L-lysine is about 5.0 mM. The final concentration of arginine is about 1 to about 40 mM, preferably about 1 to about 30, most preferably about 5 to about 15 mM. In one embodiment, the final concentration of arginine is about 10 mM.

For long term storage of cells, an effective amount of cryoprotectant may be added that allows the matrix to be stored at lower temperatures without cellular damage. Preferably, the cryoprotectant is metabolically stable and capable of creating an inert cushion to prevent thermal expansion and contraction of cells. A preferred cryoprotectant is sulfated dextran. The cryoprotectant is present at a concentration of about 0 to about 2 mM, preferably 0 to about 1 mM, most preferably about 0 to about 0.1 mM. In one embodiment, the cryoprotectant is present in a concentration of about 0.086 mM. Dextran is also useful as a nitric oxide scavenger.

Table 1 below lists particularly preferred key components of the matrix of the present invention along with suitable concentrations as well as preferred concentrations for each component.

TABLE 1

| Component | Concentration Range | Preferred Concentration |
|---|---|---|
| L-glutamic acid | 2 to 60 mM | 15 mM |
| L-lysine | .5 to 30 mM | 5.0 mM |
| Arginine | 1 to 40 | 10 mM |
| Gelatin | 0.01 to 40 mM | 1.6 mM |
| L-cysteine | 5 to 500 µM | 20 µM |
| Aminoguanidine | 5 to 500 µM | 20 µM |
| Intact collagen | 0 to 5 mM | 0.11 mM |
| EDTA | 0 to 10 mM | 4 mM |
| Albumin | 0 to 2% by volume | 0.05% by volume |
| Dextran | 0 to 2 mM | 0.086 mM |

The matrix may be used to stimulate or enhance vascularization in a mammal at an anatomic site without immune cell stimulation at the site, resulting in long term functional vascularity. That is, after insertion of the matrix in a mammal, vascularization is stimulated in tissue surrounding the matrix. "Anatomic site" is a predetermined site in a mammal where vascularization is needed.

Anatomic sites include sites of disease in an organism such as sites of chronic inflammation, atherosclerosis, sites also include sites where a transplant, including cells and/or organs will be placed within a mammal. In essence, generally any site within a mammal may be a suitable site. In particular, muscles, body cavities, particularly the abdominal or the peritoneal cavity are preferred sites.

"Vascularization" refers to the formation and maintenance of blood vessels. Stimulation or enhancement of vascularization is defined as increasing blood vessel formation and resulting blood circulation beyond that which would occur naturally.

The vascularization enhanced by the matrix is maintained in the organism. This is counter to the temporary vascular changes observed during an immune response. Inflammation is accompanied by proliferation of small blood vessels (angiogenesis). However, angiogenesis is often followed by regression or a loss of vessel structure. That is, the vessel integrity is not maintained following inflammation. In contrast, the vascularization or blood vessel formation of the invention results in mature vessels that maintain vessel integrity and survive as mature vessels. The process mimics vasculogenesis where a vascular network is established during embryogenesis. Thus, the vascularization of the invention is characterized by a network of mature blood vessels that is maintained in the host.

An effective amount of the matrix is applied to a site in a mammal where vascularization is desired. An effective amount is an amount necessary to stimulate the flow of blood to the desired anatomic site. The matrix may be used to improve vascularization at a transplant site so that a blood supply is already available for the transplanted cells, tissues, or organs in the recipient. However, matrix may be routinely applied to the transplant site at the time of the procedure with neovascularization occurring within a few days, generally about 4 to 7 days. The vascularization effect of the matrix increases the likelihood of long-term cell and organ viability in a recipient.

The methods of the invention can be used to increase vascularization in any mammal in need thereof. Mammals of interest include humans, dogs, cows, pigs, cats, sheep, horses, etc., particularly humans.

Any means may be used to apply or administer the matrix to the desired anatomic site. The amount of matrix applied will vary depending upon the amount of circulation needed (for example, the size of the organ or tissue to be implanted in the recipient, the area of the site, etc.), the weight and size of the recipient, the condition being treated, and the like. An effective amount of the matrix is an amount that promotes the desired amount of vascularization or blood flow and prevents an immune response and the formation of scar tissue.

As the matrix apparently stimulates vascularization by physical contact with tissue, the amount to be injected can be determined by (i) the linear length of tissue disruption to expose polar basement membrane sites and (ii) the volume of the disrupted tract or area to be filled with matrix.

The matrix may be used to increase vascularization in patients in need thereof. Thus, the methods of the invention are useful for the treatment of diseases or conditions that benefit from increased blood circulation, for providing a vascularized site for transplantation, for enhancing wound healing, for decreasing scar tissue formation, i.e., following injury or surgery, for conditions that may benefit from directed suppression of the immune response at a particular site, and the like.

Any condition that would benefit from increased blood flow are encompassed such as, for example, gangrene, diabetes, poor circulation, arteriosclerosis, atherosclerosis, coronary artery disease, aortic aneurysm, arterial disease of the lower extremities, cerebrovascular disease, etc. In this manner, the methods of the invention may be used to treat peripheral vascular diseases by directly injecting matrix to promote vascularization. Likewise, the matrix is useful to treat a diseased or hypoxic heart, particularly where vessels to the heart are obstructed. Injection of the matrix into the myocardium results in the formation of new blood vessels. Other organs with arterial sclerosis may benefit from an injection of the matrix. Likewise, organs whose function may be enhanced by higher vascularization may be improved by an injection of the matrix. This includes kidneys or other organs which need an improvement in function. In the same manner, other targets for arterial sclerosis include ischemic bowel disease, cerebro vascular disease, impotence of a vascular basis, and the like. Additionally, formation of new blood vessels in the heart is critically important in protecting the myocardium from the consequences of coronary obstruction. Injection of the matrix into ischemic myocardium may enhance the development of collaterals, accelerate the healing of necrotic tissue and prevent infarct expansion and cardiac dilatation.

The matrix is suitable for use in the transplantation of cells within a transplant device such as described in U.S. patent application Ser. No. 08/568,694, which is herein incorporated by reference in its entirety. A transplant device is any device designed to contain and protect cells transplanted into a host organism for the production of hormones or other factors. Examples of other transplant devices suitable for use with the matrix include those described in U.S. Pat. Nos. 5,686,091, 5,676,943 and 5,550,050. However, it is also recognized that the matrix may be used as the sole transplant vehicle without using such devices.

The methods of the invention are useful for the stimulation of new blood vessels without the presence of immune cells and the characteristic immune response. Thus, the use of the matrix of the invention results in vascularization without the formation of scar tissue. Therefore, the matrix may be utilized in any physiological setting where the formation of blood vessels is desired.

Cardiac and stroke patients may benefit by an increase in vascularization. Thus, the matrix may be used to improve circulation in post stroke or heart attack victims.

Because the matrix is beneficial in preventing or reducing the inflammatory response, it may be used to treat chronic inflammatory diseases, including rheumatoid arthritis, atherosclerosis, tuberculosis, chronic lung diseases, autoimmune diseases, particularly rheumatoid arthritis and lupus erythematosis. For treatment, the matrix is injected or applied at the site of interest. For example, to reduce arthritis, the matrix may be injected into a joint in need thereof.

As indicated previously, the matrix is useful to prepare a transplant site for tissues or organs of interest. Such organ transplants include, but are not limited to, pancreas, kidney, heart, lung, liver, etc. The matrix may also be used in combination with other implants as a surgical adhesion barrier. This finds particular use with breast implants. Coating the implant in the matrix prevents or reduces the likelihood of scar tissue formation and adhesion, thus reducing pain and inflammation following surgery. Likewise, the matrix may serve as an adjunct to provide vascularization to a cellular implant. Such cells in the implant may be native or genetically modified.

In one embodiment, cells embedded in matrix may be utilized for grafting into the central nervous system to treat defects, diseases, or damage of the central nervous system. In this manner, the matrix may be utilized in methods for intracerebral neural grafting. That is, cells which are utilized to replace or inject into the central nervous system may be contained within the matrix of the invention. Such central nervous system diseases include Parkinson's disease, Huntington's disease, Alzheimer's disease, Bipolar disease, schizophrenia, and many other major human diseases.

Methods for intracerebral grafting are known in the art. See, for example, Blacklund et al. (1985) *J. Neurosurg* 62:169–173; Madrazo et al. (1987) *New Eng. J. Med.* 316:831–36; Bjorklund et al. (1986) *Ann. N.Y. Acad. Sci.* 475:53–81; and Dunnett et al. (1983) *Trends Neurosci.* 6:266–270. See also Joyner et al. (1983) *Nature* 305:556–58; Miller et al. (1984) *Science* 225:630–632; Selden et al. (1982) *Science* 236:714–18, etc.

In this method, the matrix of the invention can be used with donor cells, including genetically modified donor cells, including fibroblasts, neurons, glial cells, keratinocytes, hepatocytes, connective tissue cells, ependymal cells, chromaffin cells, and other mammalian cells susceptible to genetic manipulation and grafting.

Following in vitro fertilization, the embryo is implanted in a female for gestation. The methods of the invention can be used to prepare a vascularized bed for transplantation. In this embodiment, matrix is injected into the uterine wall to promote blood vessel formation prior to implantation of the embryo.

Alternatively, matrix may be applied at the time of implantation to aid in vascularization.

As indicated earlier, the matrix enables vascularization without stimulating immune cells. Thus, the matrix finds use in promoting wound healing. The matrix provides new blood vessel growth and fibroblasts to the site without the attraction of immune cells. The matrix prevents inflammation while promoting wound healing. Any tissue, or site, in need of repair or healing may benefit from application of the matrix to the site. Sites include those resulting from injury or surgery. The matrix may be applied to internal, or external surgical or injury sites to reduce the pain accompanying a classic inflammatory response, and to reduce scar tissue formation.

The matrix is also beneficial for superficial wound healing. Thus, it may be useful to apply to skin ulcers, burn areas, ulcers that form secondary to peripheral vascular disease, or other tissue damage.

The following examples are offered by way of illustration and not by way of limitation.

EXPERIMENTAL

Matrix Preparation

Place 835 ml of Medium 199 into a stirred beaker. While stirring, heat the solution to 50° C. Using a syringe, add 20 ml of albumin to the stirred solution. Pipette 63.28 $\mu$l of cysteine, 1 ml of L-glutamine and 200 $\mu$l of aminoguanidine into the stirred beaker. Add the following gamma irradiated dry raw materials: 120 grams of denatured collagen, 50 grams of dextran, and 0.1 grams of intact collagen. Use a glass stirring rod to aid mixing of the dry materials into solution. Pipette 8 ml of EDTA into the solution. Pipette 5 ml of L-glutamic acid, 5 ml of L-lysine acetate, and 5 ml of arginine HCl into the stirred beaker. Note that the solution will turn yellow. Use 10% NaOH to adjust the pH of the matrix solution to a final pH of 7.40±0.05.

Cells may be embedded in the matrix of the present invention using the following procedure. Aspirate the supernatant from centrifuged cell pellets. Add a volume of cell culture medium and matrix to the cell pellets. Add a volume of matrix approximately equal to about 4 times the pellet volume. Add a volume of cell culture medium to the cell pellets equaling approximately 0.05 times the matrix volume added. Store the encapsulated cells at refrigerated temperatures if not using immediately.

Example 1

Figure 2:
FIG. 2 shows a vascularized device sheath 16 weeks post implant in a diabetic dog.

Normal 200–300 gram rats were injected intramuscularly with enhanced matrix. The animals were sacrificed at 4–6 days, and 21 days. Histologic sections revealed copious fibroblasts and new blood vessel formation at the injection site. Notably absent was the presence of immune or inflammatory cells. When placed around ENCELLIN XP devices, manufactured by Encelle, Inc., a thin fibrous capsule forms around the device which remains vascularized for the duration of the implant (out to four months in dogs and six months in rabbits). A non-adherent fibrous sheath with blood vessels was apparent at time of explant four months after surgical implantation in the dog. FIG. 1 shows blood vessel formation 6 weeks post implant where a bioartificial pancreas that has a bioactive surface (tissue in matrix placed in wells covered by parylene N) was implanted between muscle layers with matrix liberally applied over the front and back. FIG. 2 shows a vascularized device sheath 16 weeks post implant in a diabetic dog.

Example 2

The ability of the matrix of the present invention to stimulate blood vessels inn a fibrous capsule was compared to matrigel with or without bFGF or VEGF when applied around polycarbonate devices intermuscularly in rats. Devices surrounded by these materials or no material were removed from some rats at 21 days and some at 50 days. bFGF and VEGF are two angiogenic growth factors currently in human clinical trials. Polycarbonate disks were implanted submuscularly in rats. The implants were removed after 21 and 50 days, stained with H&E, and Masson's Trichrome. The capsule thickness and vascular density of the capsule were evaluated.

| Abbreviation | Description |
|---|---|
| Uninvolved | Undisturbed tissue from the implant site |
| UPC | Uncoated polycarbonate disk |
| Coated | Polycarbonate disk coated with parylene |
| Matrigel | Parylene coated disk embedded in matrigel |
| VEGF | Parylene coated disk embedded in Matrigel + 3000 ng/ml VEGF (Vascular Endothelial Growth Factor) |
| BFGF | Parylene coated disk embedded in Matrigel + 3000 ng/ml bFGF (basic fibroblast growth factor) |
| EM | Parylene coated disk embedded in matrix of present invention |
| EM+ | Parylene coated disk embedded in matrix of present invention (including supplemental polar amino acids) |
| RS | Parylene coated disk embedded in matrix of present invention (including 10% rat serum) |
| RS+ | Parylene coated disk embedded in matrix of present invention (including supplemental polar amino acids and 10% rat serum) |

Only the matrix of the present invention stimulated new blood vessel growth between 21 and 50 days post injection. While all other groups stimulated initial new blood vessel growth up to 21 days, a diminution in both blood vessel number and fibrous capsule thickness was documented as mature scar tissue was formed. In addition, the matrix treated animals did not show the immune cell/inflammatory response observed in the bFGF and VEGF treated animals. See, FIGS. 3 and 4.

Figure 3:
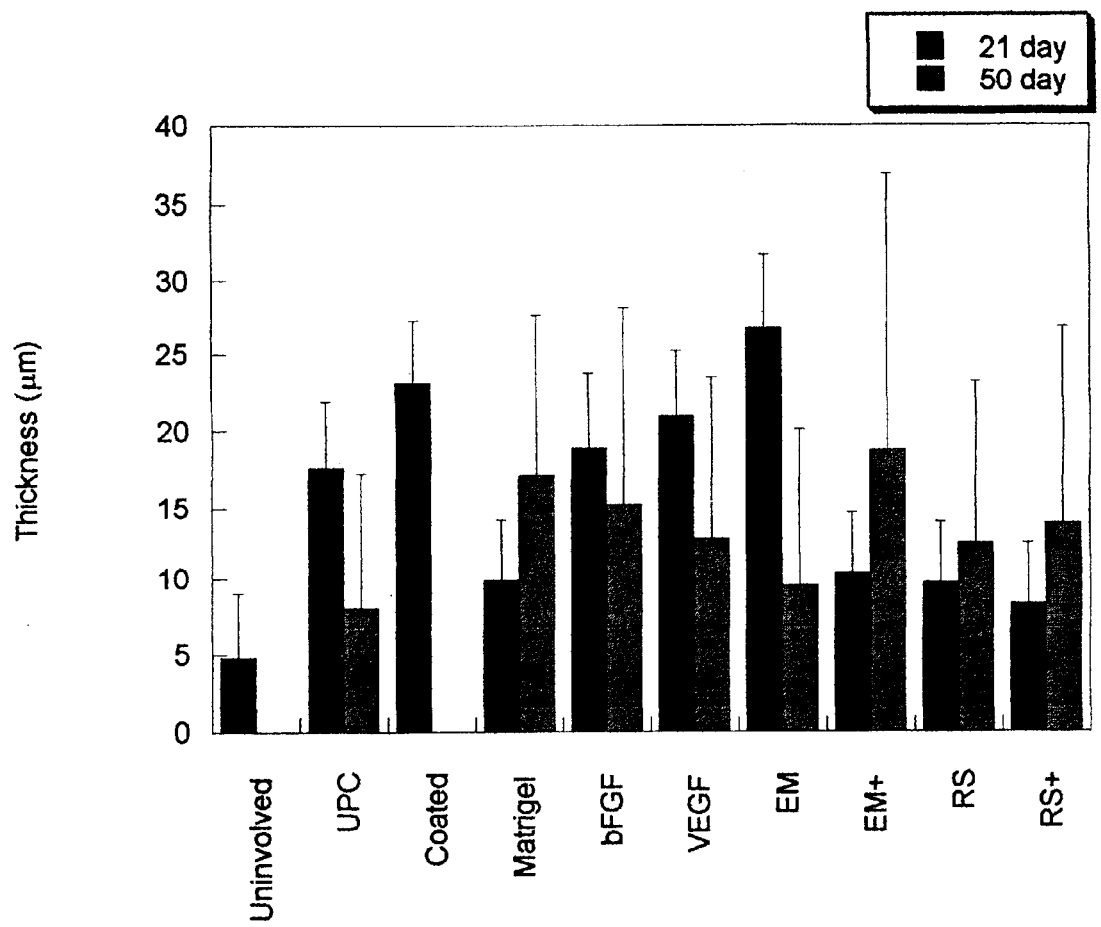
FIG. 3 provides a graph indicating capsule thickness after 21 and 50 days of implantation.

FIG. 3 shows that after 21 days of implantation, the capsule thickness around the implanted devices were significantly ($p<0.05$) lower in the EM+, RS, and RS+ treated samples when compared to the coated polycarbonate disks (control). Disks coated with just Matrigel also showed a significantly ($p<0.05$) lower capsule thickness than the control. The presence of growth factors seems to eliminate any reduction in capsule thickness with pure Matrigel. After 50 days of implantation, no significant differences in capsule thickness with pure Matrigel. After 50 days of implantation, no significant differences in capsule thickness were observed in any treatment group.

Figure 4:
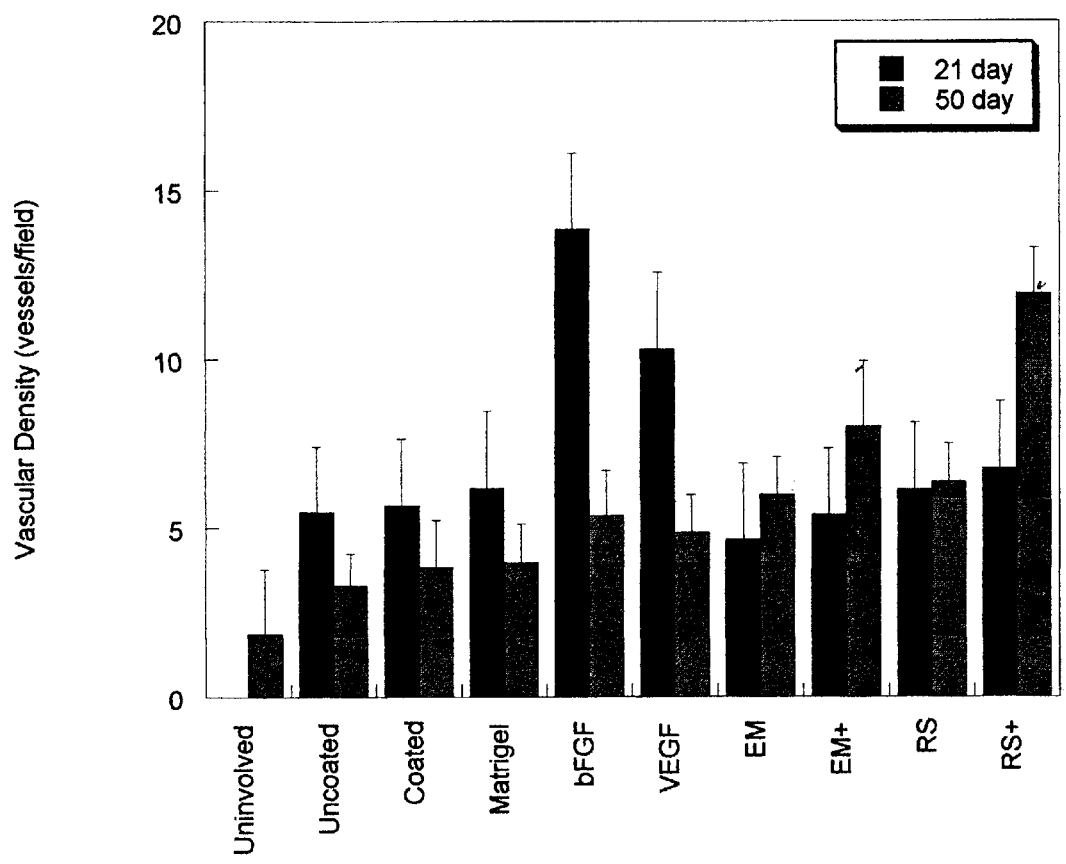
FIG. 4 provides a graph indicating vascular density after 21 and 50 days of implantation.

FIG. 4 shows that after 21 days of implantation, the observed vascular density surrounding the implanted disks as essentially the same for all treatments except for those with growth factors present. After 50-days of implantation, the additional vascular density observed with the growth-factor-enhanced Matrigel implants disappears. The vascular density of the implants with no matrix and the Matrigel covered implants decreased from 21 to 50 days. On the other hand, the vascular density provided by the matrices of the present invention (EM, EM+, RS, and RS+) all remained the same or increased.

The matrix can be applied to any area where new, physiologic vascularization is required. It can serve as an adjunct to provide vascularization to an implanted drug delivery or cell system, or can be used to enhance vascularization at a pathologic site. Such examples of the latter would be in diabetic peripheral vascular disease, cerebral ischemia, ischemic heart disease, Raynaud's phenomenon, or post-stroke.

The matrix might also prove useful in surgical applications where a minimization of scar tissue is desired. Because a thin fibrous capsule is formed that remains vascularized, the matrix may be applied to surgical breast implants to minimize painful adhesions.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of stimulating vascularization at a site in a mammal, said method comprising:

contacting said site with a matrix comprising gelatin and a nitric oxide inhibitor.

2. The method of claim 1, wherein the matrix further comprises a nitric oxide scavenger.

3. The method of claim 2, wherein said nitric oxide scavenger is a sulfonated moiety.

4. The method of claim 1, wherein said nitric oxide inhibitor is an L-arginine analog.

5. The method of claim 2, wherein said nitric oxide scavenger is selected from the group consisting of dextran, heparin, cysteine and cystine.

6. The method of claim 4, wherein said L-arginine analog is selected from the group consisting of aminoguanidine, N-monoethyl L-arginine, N-nitro-L-arginine and D-arginine.

7. The method of claim 1, wherein the matrix further comprising an effective amount of polar amino acids, said polar amino acids selected from the group consisting of arginine, lysine, histidine, glutamic acid, and aspartic acid.

8. The method of claim 7, wherein said effective amount of polar amino acids comprises about 3 to about 150 mM of polar amino acids.

9. The method of claim 7, wherein said polar amino acids are selected from the group consisting of arginine, glutamic acid, lysine or mixtures thereof.

10. The method of claim 1, wherein said gelatin comprises denatured collagen.

11. The method of claim 1, wherein said matrix further comprises native collagen.

12. The method of claim 10, wherein said matrix comprises about 0.01 to about 40 mM denatured collagen.

13. The method of claim 1, wherein said matrix further comprises:

about 2 to about 60 mM of L-glutamic acid;

about 0.5 to about 30 mM of L-lysine; and about 1 to about 40 mM of arginine.

14. The method of claim 1, wherein said matrix further comprises about 5 to about 500 $\mu$M of L-cysteine.

15. The method of claim 4, wherein said matrix comprises about 5 to about 500 $\mu$M of L-arginine analog.

16. The method of claim 15, wherein said L-arginine analogue is aminoguanidine.

17. A method for treating vascular disorders, said method comprising administering an effective amount of a matrix to an anatomic site that is in need of increased blood flow, wherein said matrix comprises gelatin and a nitric oxide inhibitor.

18. The method of claim 17, wherein the matrix further comprises a nitric oxide scavenger.

19. The method of claim 18, wherein said nitric oxide scavenger is a sulfonated moiety.

20. The method of claim 17, wherein said nitric oxide inhibitor is an L-arginine analog.

21. The method of claim 18, wherein said nitric oxide scavenger is selected from the group comprising dextran, heparin, cysteine and cystine.

22. The method of claim 20, wherein said L-arginine analog is selected from the group consisting of aminoguanidine, N-monoethyl L-arginine, N-nitro-L-arginine and D-arginine.

23. The method of claim 17, further comprising an effective amount of polar amino acids, said polar amino acids selected from the group consisting of arginine, lysine, histidine, glutamic acid, and aspartic acid.

24. A method according to claim 23, wherein said effective amount of polar amino acids comprises about 3 to about 150 mM of polar amino acids.

25. A method according to claim 23, wherein said polar amino acids are selected from the group consisting of arginine, glutamic acid, lysine or mixtures thereof.

26. A method of stimulating vascularization at a site in a mammal, said method comprising;
contacting said site with a matrix comprising gelatin, dextran and a nitric oxide inhibitor.

27. The method of claim 26, wherein said gelatin is denatured collagen.

28. The method of claim 27, wherein said matrix comprises about 0.01 to about 40 mM denatured collagen.

29. The method of claim 26, wherein said matrix comprises about 0 to about 2 mM dextran.

30. The method of claim 26, wherein said nitric oxide inhibitor comprises an L-arginine analogue.

31. The method of claim 30, wherein said L-arginine analogue is aminoguanidine.

32. The method of claim 31, wherein said matrix comprises about 5 to about 500 µM aminoguanidine.

33. The method of claim 26, wherein the matrix further comprises a nitric oxide scavenger selected from the group comprising heparin, cysteine and cystine.

34. The method of claim 26, wherein the matrix further comprises about 5 to about 500 µM L-cysteine.

35. The method of claim 26, wherein the matrix further comprises an effective amount of polar amino acids, said polar amino acids selected from the group consisting of arginine, lysine, histidine, glutamic acid, and aspartic acid.

36. The method of claim 35, wherein said effective amount of polar amino acids comprises about 3 to about 150 mM of polar amino acids.

37. The method of claim 35, wherein said matrix comprises:
about 2 to about 60 mM of L-glutaimic acid;
about 0.5 to about 30 mM of L-lysine; and
about 1 to about 40 mM of arginine.

38. A method of stimulating vascularization at a site in a mammal, said method comprising;
contacting said site with a matrix comprising gelatin, dextran, a nitric oxide inhibitor and an effective amount of polar amino acids, said polar amino acids selected from the group consisting of arginine, lysine, histidine, glutamic acid, and aspartic acid.

39. The method of claim 38, wherein the matrix further comprises about 5 to about 500 µM L-cysteine.

40. The method of claim 38, wherein said nitric oxide inhibitor comprises an L-arginine analogue.

41. The method of claim 38, wherein said nitric oxide inhibitor comprises about 5 to about 500 µM aminoguanidine.

42. The method of claim 38, wherein said effective amount of polar amino acids comprises about 3 to about 150 mM of polar amino acids.

43. The method of claim 38, wherein said matrix comprises:
about 2 to about 60 mM of L-glutamic acid;
about 0.5 to about 30 mM of L-lysine; and about 1 to about 40 mM of arginine.

44. The method of claim 38, wherein said gelatin comprises about 0.0 1 to about 40 mM denatured collagen.

45. The method of claim 38, wherein said matrix comprises about 0 to about 2 mM dextran.

46. A method of stimulating vascularization at a site in a mammal, said method comprising:
contacting said site with a matrix comprising denatured collagen, dextran, aminoguanidine and an effective amount of polar amino acids, said polar amino acids selected from the group consisting of arginine, lysine, and glutamic acid.

47. The method of claim 46, wherein said matrix comprises:
about 0 and about 2 mM dextran;
about 0.01 to about 40 mM denatured collagen;
about 5 to about 500 µM aminoguanidine;
about 2 to about 60 mM of L-glutamic acid;
about 0.5 to about 30 mM of L-lysine; and
about 1 to about 40 mM of arginine.

48. A method for treating vascular disorders, said method comprising administering an effective amount of a matrix to an anatomic site that is in need of increased blood flow, wherein said matrix comprises gelatin, dextran and a nitric oxide inhibitor.

49. A method of claim 48, wherein said gelatin comprises about 0.01 to about 40 mM denatured collagen.

50. A method of claim 48, wherein said matrix comprises about 0 to about 2 mM dextran.

51. A method of claim 48, wherein said nitric oxide inhibitor comprises an L-arginine analogue.

52. The method of claim 48, wherein said nitric oxide inhibitor comprises about 5 to about 500 µM aminoguanidine.

53. The method of claim 48, wherein the matrix further comprises about 5 to about 500 µM L-cysteine.

54. The method of claim 48, wherein the matrix further comprises an effective amount of polar amino acids, said polar amino acids selected from the group consisting of arginine, lysine, histidine, glutamic acid, and aspartic acid.

55. A method according to claim 54, wherein said effective amount of polar amino acids comprises about 3 to about 150 mM of polar amino acids.

56. The method of claim 48, wherein said matrix comprises:
about 2 to about 60 mM of L-glutamic acid;
about 0.5 to about 30 mM of L-lysine; and
about 1 to about 40 mM of arginine.

57. The method of claim 48, wherein said matrix comprises:
about 0 and about 2 mM dextran;
about 0.01 to about 40 mM denatured collagen;
about 5 to about 500 µM aminoguanidine;
about 2 to about 60 mM of L-glutamic acid;
about 0.5 to about 30 mM of L-lysine; and
about 1 to about 40 mM of arginine.

* * * * *

UNITED STATES PATENT AND TRADEMARK OFFICE
CERTIFICATE OF CORRECTION

PATENT NO. : 6,261,587 B1
DATED : July 17, 2001
INVENTOR(S) : Usala

It is certified that error appears in the above-identified patent and that said Letters Patent is hereby corrected as shown below:

<u>Title page,</u>
Item [56], References Cited, OTHER PUBLICATIONS,
Line 2, after "Porcine" insert -- Islets --;
Line 10, "Allograftting" should read -- Allografting --.

U.S. PATENT DOCUMENTS,
Last line, "Kuberasampeth et al." should read -- Kuberasampath et al. --

<u>Column 2,</u>
Line 5, "10/1998" shold read -- 11/1998 --.

<u>Column 10, claim 7,</u>
Line 30, "comprising" should read -- comprises --.

<u>Column 11, claim 26,</u>
Line 19, after "comprising" the semi-colon (;) should be a colon (:).

<u>Column 11, claim 37,</u>
Line 48, "glutaimic" should read -- glutamic --.

<u>Column 12, claim 44,</u>
Line 7, "0.0 1" should read -- 0.01 -- (no space).

Signed and Sealed this

Twenty-fifth Day of December, 2001

*Attest:*

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO. : 6,261,587 B1
DATED : July 17, 2001
INVENTOR(S) : Usala

It is certified that error appears in the above-identified patent and that said Letters Patent is hereby corrected as shown below:

Title page,
Item [56], References Cited, OTHER PUBLICATIONS, after "Porcine" insert -- Islets --;
Line 10, "Allograftting" should read -- Allografting --.

Title page 2, column 1,
Item [56], References Cited, U.S. PATENT DOCUMENTS,
Last line "Kuberasampeth et al." should read -- Kuberasampath et al. --;

Title page 2, column 2,
Line 5, "10/1998" should read -- 11/1998 --.

Column 10, claim 7,
Line 30, "comprising" should read -- comprises --.

Column 11, claim 26,
Line 19, after "comprising" the semi-colon (;) should be a colon (:).

Column 11, claim 37,
Line 48, "glutaimic" should read -- glutamic --.

Column 12, claim 44,
Line 7, "0.0 1" should read -- 0.01 -- (no space).

Signed and Sealed this

Twenty-ninth Day of January, 2002

Attest:

*Attesting Officer*

JAMES E. ROGAN
*Director of the United States Patent and Trademark Office*